US008669114B2

(12) United States Patent
Sundermeyer et al.

(10) Patent No.: US 8,669,114 B2
(45) Date of Patent: Mar. 11, 2014

(54) HYDROPHOBIC IONIC LIQUIDS

(75) Inventors: Jorg Sundermeyer, Marburg (DE); Thomas Linder, Calgary (CA)

(73) Assignee: Philipps-Universitaet Marburg, Marburg (DE)

( * ) Notice: Subject to any disclaimer, the term of this patent is extended or adjusted under 35 U.S.C. 154(b) by 745 days.

(21) Appl. No.: 12/227,351

(22) PCT Filed: May 17, 2007

(86) PCT No.: PCT/DE2007/000892
§ 371 (c)(1),
(2), (4) Date: Mar. 13, 2009

(87) PCT Pub. No.: WO2007/131498
PCT Pub. Date: Nov. 22, 2007

(65) Prior Publication Data
US 2009/0298189 A1    Dec. 3, 2009

(30) Foreign Application Priority Data

May 17, 2006    (DE) .......................... 10 2006 023 649

(51) Int. Cl.
| | |
|---|---|
| B01J 20/22 | (2006.01) |
| B01J 20/281 | (2006.01) |
| C07C 211/63 | (2006.01) |
| C07C 211/03 | (2006.01) |
| C07C 233/06 | (2006.01) |
| C07C 233/54 | (2006.01) |
| C07C 233/56 | (2006.01) |
| H01M 10/052 | (2010.01) |
| C07D 233/06 | (2006.01) |
| C07D 235/08 | (2006.01) |
| C07D 213/20 | (2006.01) |
| G01N 30/00 | (2006.01) |

(52) U.S. Cl.
USPC ........... 436/161; 429/188; 429/324; 429/339; 429/341; 546/347; 548/304.4; 548/347.1; 564/291

(58) Field of Classification Search
None
See application file for complete search history.

(56) References Cited

U.S. PATENT DOCUMENTS

| 3,920,444 A | 11/1975 | Harrington et al. |
|---|---|---|
| 4,173,463 A * | 11/1979 | Peterson et al. ............. 504/207 |
| 5,827,602 A | 10/1998 | Koch et al. |

FOREIGN PATENT DOCUMENTS

| DE | 102 58 671 A1 | 6/2004 |
|---|---|---|
| DE | 696 29 816 | 7/2004 |
| DE | 103 33 239 | 3/2005 |
| DE | 10 2004 034 543 | 2/2006 |
| EP | 0 839 139 | 9/2003 |
| EP | 1 414 088 | 4/2004 |
| FR | 2 795 725 | 5/2001 |
| GB | 2 418 926 A | 4/2006 |
| JP | 2005-314332 | 11/2005 |
| WO | 97/02252 | 1/1997 |
| WO | 01/03211 | 1/2001 |
| WO | 01/77081 | 10/2001 |
| WO | 03/087110 A1 | 10/2003 |
| WO | 2004/054991 | 7/2004 |
| WO | 2005/075413 A1 | 8/2005 |
| WO | 2006/021302 A1 | 3/2006 |
| WO | 2006/021303 A1 | 3/2006 |
| WO | 2006/021304 A1 | 3/2006 |

OTHER PUBLICATIONS

Kondo et al., Tetrahedron 56, 2000, 5843-5856.*
AmmoniumSalt, 2012, http://www.alibaba.com/showroom/ammonium-salt-pesticide-herbicide.html.*
Guthner et al., Ullmann's Encyclopedia of Industrial Chemistry, vol. 17, p. 175-188, 2012.*
Malek et al., http://www.sciencedirect.com/science/article/pii/S0924203106001196, 2006.*
Taylor et al, 1979, https://data.epo.org/publication-server/html-document?PN=EP0006359%20EP%200006359&iDocId=4257970.*
R. Koppang, *Acta Chemica Scandinavica*, 25, (1971) No. 8, pp. 3067-3071.
A. Khvorost et al., "Lithium *Bis*(pentafluorophenyl)amide—Syntheses and Structural Characterization of its Complexes with Diethyl Ether and THF", *Z. Anorg. Allg. Chem.*, 2004, 630, pp. 885-889.
Y. Chiang et al., "Flash Photolytic Generation of Primary, Secondary, and Tertiary Ynamines in Aqueous Solution and Study of Their Carbon-Protonation Reactions in That Medium", *J. Am. Chem. Soc.*, 1996, 118, pp. 4366-4372.
A. Nagy et al., "He(I) and He(II) photoelectron spectroscopic investigation of substituent effects in aminosilanes", (1991) *Journal of Organometallic Chemistry*, 419, pp. 27-42.
R. Koppang, "Poly-*N*-Methyliminotetrafluro-1,4-Phenylene", (1976) *Journal of Polymer Science*, vol. 14, pp. 2225-2231.
V.M. Vlasov et al., Chemical Abstracts Service, "Polyfluoraryl-containing N-anions, proton and fluorine-19 NMR spectra of their salts" (1981) *Zhurnal Organicheskoi Khimii*, 17(10), 2192-201 (XP-002453414).

* cited by examiner

*Primary Examiner* — Sun Jae Loewe
(74) *Attorney, Agent, or Firm* — Clark & Brody

(57) ABSTRACT

The subject of the invention at hand are novel, a little basic, fluorinated pentafluorophenyl imide anions, which can be used as anions in ionic liquids. Methods for producing ionic liquids are described, which contain these novel pentafluorophenyl imide ions as anions, as well as quaternary organic ammonium ions, guanidinium ions, N-organo-pyridinium ions, imidazolium, imidazolidinium or benzimidazolidinium ions, alkyl-alkylidene phosphoranes or aryl-alkylidene phosphoranes as cations. Alternative methods according to the present invention provide ionic liquids through reaction of ketene N,N-diacetals or alkyl or aryl-alkylidene phosphoranes with acids.

Figure 1:
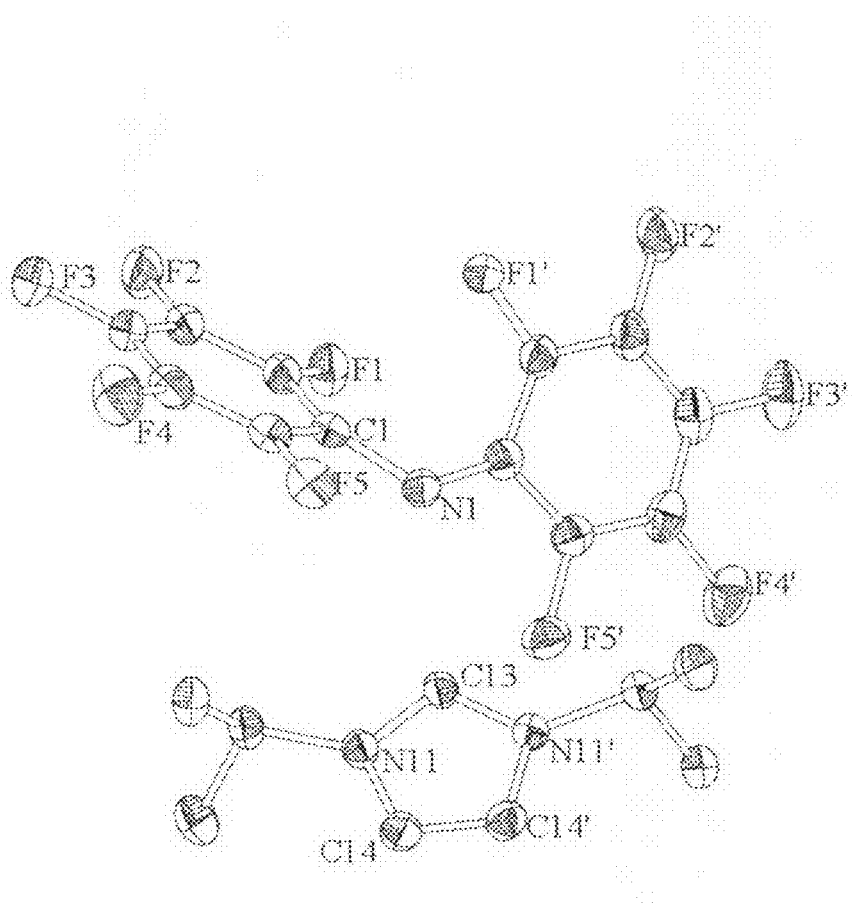

The ionic liquids according to the present invention are suitable, for example, as solvents for syntheses, as mobile and/or stationary phase in chromatography, as electrolyte systems for batteries, galvanic elements, fuel cells and rechargeable battery packs.

21 Claims, 2 Drawing Sheets

HYDROPHOBIC IONIC LIQUIDS

The invention at hand concerns salts of pentafluorophenyl imide anions and any cations, a method for their production, as well as their use as hydrophobic ionic liquids.

DESCRIPTION AND INTRODUCTION TO THE GENERAL ASPECTS OF THE INVENTION

The invention at hand concerns the areas of electrochemistry, material chemistry, organic chemistry and reaction technology.

TECHNICAL STATE OF THE ART

Ionic liquids are compounds which are comprised of an organic cation and an inorganic or organic anion. They do not contain any neutral molecules and have melting points under 100° C. In the technical state of the art, many compounds are known which are used as ionic liquids. In particular, they are also the subject of various patents or patent applications.

Several of these publications describe hydrophobic ionic liquids, wherein it is often attempted to increase the hydrophobicity through the introduction of halogen atoms or long alkyl chains into anions or cations. Thus, JP 2005 314 332 A1 discloses ionic liquids whose anions contain fluoroalkylsulfates. DE 103 33 239 A1 describes ionic liquids whose anions can be, amongst others, bis-(perfluoroalkylsulfonyl) imides $[N(SO_2Rf)_2]^-$ or tris-(perfluoroalkylsulfonyl)methides $[C(SO_2Rf)_3]^-$. DE 102 58 671 A1 discloses ionic liquids with bis-(trifluoromethyl)-imide anions.

It is known to persons skilled in the art that dipentafluorophenyl amine is very hydrophobic and a little basic. This compound can be produced according to R Koppang, Acta Chem. Scand 1971, 3067-3071 by reaction of $C_6F_6$ with a metal amide, preferably $LiNH_2$ according to the subsequent reaction equations (also as one pot reaction $LiNH_2 + C_6F_6 \rightarrow LiF + H_2N-C_6F_5$ $H_2C_6F_5 + LiNH_2 \rightarrow LiNH-C_6F_5 + NH_3$ $2LiNHC_6F_5 + C_6F_6 \rightarrow LiN(C_6F_5)_2 + H_2C_6F_5 + LiF$ $LiN(C_6F_5)_2 + HX \rightarrow HN(C_6F_5)_2 + LiX$ In this, X stands, for example, for a halogen atom, nitrate, hydrogen sulfate or dihydrogen phosphate.

In the technical state of the art, however, no indications exist regarding the suitability of dipentafluorophenyl amine and its conjugate anion (dipentafluorophenyl anilide or decafluorodiphenyl imide) for producing ionic liquids.

Ionic liquids are used, for example as components of electrolyte systems in batteries, rechargeable battery packs, galvanic elements and fuel cells or as solvents in syntheses.

Several known ionic liquids contain imidazolium cations. These ionic liquids are particularly advantageous when used as solvents for noble metal catalyzed syntheses. Thus, DE 10 2004 034 543 A1 describes, for example, a method for producing onium salts with low chloride content as cations in ionic liquids. These cations can be, amongst others, imidazolium cations, including 2H-imidazolium cations. Furthermore, WO 01/77081 A1 describes a method for producing 2H-imidazolium salt-based ionic liquids through the reaction of an acid or an alcohol with nucleophilic N-heterocyclic carbene precursors. Ionic liquids, which are based on 2H-imidazolium cations, are, on the one hand, very good solvents for noble metal catalyzed syntheses. On the other hand, they have the disadvantage that, above all in the presence of platinum catalysts, C—H activation at the C2 atom of the imidazolium cation occurs easily with the oxidative addition to the noble metal center and the formation of a carbene complex. This often leads to an undesired loss of activity of the catalyst. 2-alkyl-imidazolium-based ionic liquids are more stable in this regard.

The characteristics of ionic liquids, e.g. melting point, thermal and electrochemical stability and viscosity, are strongly influenced by the nature of the anion. In contrast, the polarity and the hydrophilicity or lipophilicity can be varied through suitable choice of the cation/anion pair.

The purity of ionic liquids is of high importance when they are used. Impurities in ionic liquids can, for example, negatively influence the process of chemical reactions. Thus, methods are required which allow for the introduction of an anion through quantitative chemical reaction and not through shifting of the equilibrium during ion exchange. Furthermore, new, outwardly hydrophobic/lipophilic ionic liquids at the end of the polarity scale are largely required, which offer new possibilities regarding their use in multiphase catalysis (immiscible with water) or in electrochemical and analytic applications.

AIM OF THE INVENTION

The aim of the invention at hand is to provide salts comprising new, a little basic fluorinated imide anions, which can be used as anions in ionic liquids, as well as methods for their production, wherein anions, in which the $pK_A$-value of the conjugate acid, measured in DMSO, is smaller or equal to 15, are understood to be a little basic.

A further aim of the invention at hand is to provide ionic liquids comprising the new, a little basic fluorinated imide ions as anions and imidazolium ions, imidazolidinium ions, benzimidazolium ions, alkyl-alkylidene phosphoranes, or aryl-alkylidene phosphoranes as cations, as well as methods for their production.

ACHIEVEMENT OF THE AIM

The aim of providing salts, comprising a little basic, fluorinated imide anions is achieved through compounds containing a) an anion of the general formula

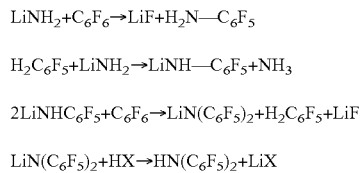

(I)

wherein

R¹ stands for a linear or branched, non-fluorinated, partially or completely fluorinated alkyl group with 1 to 20 C atoms, non-fluorinated, partially or completely fluorinated aryl group, a 2-nitroaryl group, a 4-nitroaryl group, a 2,4-dinitroaryl group, a non-fluorinated, partially or completely fluorinated benzyl group, or represents CN, CO—H, a CO-aryl group or a CO-alkyl group or represents $R^1 = -SO_2-R^2$, wherein R₂ represents a branched or unbranched alkyl group with 1 to 20 C atoms or an aryl group or benzyl group and this alkyl group, benzyl group or aryl group is non-fluorinated, partially or completely fluorinated;

and b) a cation, chosen from
inorganic cations from the group of alkali cations and earth alkali cations or quaternary organic cations.

Surprisingly, it was found that salts comprising the fluorinated imide anions 1, which contain a pentafluorophenyl group, are a little basic and stable in the form of free ions in contrast to the imide anions previously known. Free ions are hereby understood to be ions which are available, in crystalline or melted state, completely dissociated in an anion-cation pair. Imide anions, in which the $pK_A$-value of the conjugate acid is smaller or equal to 15, are understood to be a little basic. Thus, the imide anions according to the present invention are suitable for producing ionic liquids.

Anions $^-N(C_6F_5)R^1$ according to the present invention, in which $R^1$ and $R^2$ are as defined above, are preferably more than mono-fluorinated. Such anions $^-N(C_6F_5)R^1$, in which $R^1$ and $R^2$ are as defined above and in which alkyl, aryl or benzyl groups are perfluorinated, are particularly preferable.

Optionally, the R groups indicated above for $R^1$ or $R^2$, in the case where alkyl groups, aryl groups or benzyl groups are involved in this, can carry, on their sides, one to two substituents, chosen from alkyl groups and aryl groups.

If $R^1$ or $R^2$ stands for an alkyl group, aryl group or benzyl group and further alkyl groups are bound to this alkyl group, aryl group or benzyl group, then these further alkyl groups can be linear or branched and contain 1 to 20 C atoms.

If $R^1$ or $R^2$ stand for an alkyl group, aryl group or benzyl group and further alkyl groups or aryl groups are bound to this alkyl group, aryl group or benzyl group, then these further alkyl groups or aryl groups can furthermore be partially or completely fluorinated.

If $R^1$ or $R^2$ stand for an alkyl group, aryl group or benzyl group and two further alkyl groups or two further aryl groups are bound to this alkyl group, aryl group or benzyl group, then both of these further alkyl groups or both of the further aryl groups can be identical or different.

It must be emphasized that the compound $HN(C_6F_5)_2$ is actually known, however, its use for producing ionic liquids is new.

Ionic liquids, which contain $^-N(C_6F_5)R^1$ anions, wherein $R^1$ is as defined above, feature a lower viscosity and lower melting points as the technical state of the art. Furthermore, they are less volatile and possess a highly intrinsic lipophilicity and solubility for organic substrates or, respectively, a high hydrophobicity, i.e. immiscibility with, respectively, low saturation concentration regarding water.

The reason for these advantageous characteristics is the pentafluorophenyl group, which is able to be more easily polarized in comparison to perfluoroalkyl groups and perfluoroalkylsulfonyl groups.

Organic cations are preferably chosen from the group of quaternary ammonium ions, phosphonium ions, guanidium ions, imidazolium ions, imidazolidinium ions, benzimidazolium ions and n-organo-pyridinium ions.

Ammonium ions are particularly preferably chosen from compounds of the formula $$[NR^3R^4R^5R^6]^+ \quad (II),$$

wherein
$R^3$, $R^4$ and $R^5$ represent, independently from one another, a linear or branched alkyl group with 1 to 20 C atoms or an aryl group or a benzyl group and
$R^6$ represents a linear or branched alkyl group with 1 to 20 C atoms.

Phosphonium ions are particularly preferably chosen from compounds of the formula $$[PR^3R^4R^5R^7]^+ \quad (III),$$

wherein $R^3$, $R^4$ and $R^5$ have the definitions stated above and
$R^7$ represents a linear or branched alkyl group with 1 to 20 C atoms or an aryl group or a benzyl group.

Guanidinium ions are particularly preferably chosen from compounds of the formula

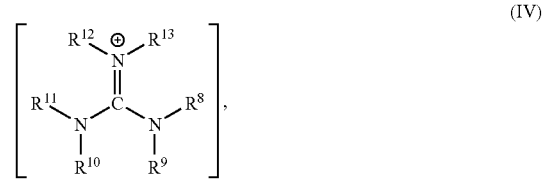

(IV)

wherein
$R^8$, $R^9$, $R^{10}$, $R^{11}$, $R^{12}$ and $R^{13}$ represent, independently from one another, an H atom or a linear or branched alkyl group with 1 to 20 C atoms or an aryl group.

In the context of the invention at hand, such guanidinium ions, in which $R^8$, $R^9$, $R^{10}$, $R^{11}$, $R^{12}$ and $R^{13}$ represent, independently from one another, a linear or branched alkyl group with 1 to 20 C atoms, are particularly preferable.

Imidazolium ions are preferably chosen from ions of the general formula

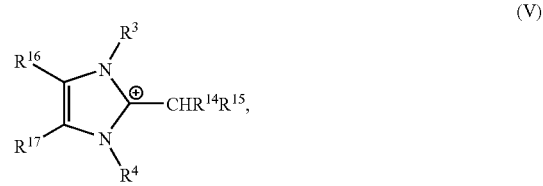

(V)

wherein
$R^3$ and $R^4$ are as defined above and
$R^{14}$, $R^{15}$, $R^{16}$ and $R^{17}$ stand, independently from one another, respectively, for an H atom, a branched or unbranched alkyl group with 1 to 20 C atoms, an aryl or a benzyl group.

Imidazolidinium ions are preferably chosen from ions of the general formula

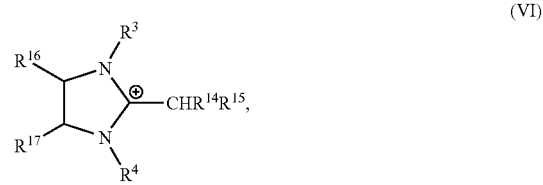

(VI)

wherein $R^3$, $R^4$, $R^{14}$, $R^{15}$, $R^{16}$ and $R^{17}$ are as defined above.

Benzimidazolium cations are preferably chosen from ions of the general formula

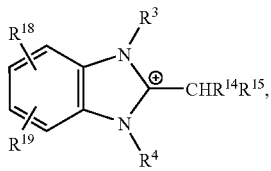
(VII)

wherein $R^3$, $R^4$, $R^{14}$ and $R^{15}$ are as defined above and $R^{18}$ and $R^{19}$ stand, independently from one another for an H atom, F, Cl, a linear or branched alkyl group with 1 to 20 C atoms, an aryl group or a benzyl group.

N-organo-pyridinium ions are preferably chosen from cations of the general formula

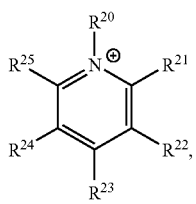
(IX)

wherein
$R^{20}$ represents a linear or branched alkyl group with 1 to 20 C atoms, an aryl group or a benzyl group, and
$R^{21}$, $R^{22}$, $R^{23}$, $R^{24}$ and $R^{25}$ represent, independently from one another, an H atom, F, Cl or a linear or branched alkyl group with 1 to 20 C atoms.

In the context of the invention at hand, such n-organo pyridinium ions, in which R20
$R^{20}$ represents a branched or unbranched alkyl group with 1 to 20 C atoms, are particularly preferable.

Such salts according to the present invention, in which $R^1$ of the $^-N(C_6F_5)R^1$ anion is a fluorinated phenyl group, naphthyl group, arylsulfonyl group or alkylsulfonyl group according to the definition above, are preferably used in ionic liquids.

If an imidazolium ion, imidazolinium ion or benzimidazolium ion is chosen as cation of an ionic liquid according to the present invention, then such cations are preferable in which the R groups $R^3$ and $R^4$ are different according to the definition stated above.

If, in contrast, an ammonium ion or phosphonium ion is chosen as cation, then asymmetrically substituted ions according to the formulas (II) or (III) stated above are preferable. Such ammonium ions or phosphonium ions, in which the R groups $R^3$, $R^4$, $R^5$, $R^6$ or $R^7$ are chosen according to the definitions above in such a way that the cation does not comprise a mirror axis perpendicular to the molecular level, are understood to be unsymmetrically substituted.

The aim of providing a method for producing non-basic perfluorinated bis(organyl) amides is achieved according to the present invention through the reaction of the pentafluorophenyl anilide(2-) synthon $[N-C_6F_5]^{2-}$ with
a) a fluoroaromatic as C-electrophile, wherein fluoride serves as the leaving group, or
b) a sulfonic acid derivative in an organic solvent.

This occurs according to the present invention by reaction of $H_2N-C_6F_5$ with a metallation reagent (metal amide, metal hydride, metal alkyl, metal hydroxide, metal carbonate, metal (elemental)/metal preferably alkali or earth alkali metal).

Subsequent reaction of the metallated anilide $M-NH-C_6F_5$, wherein "M" stands for metal, with an electrophile
from the group of $R^2$-substituted sulfonic acid chlorides, fluorides, esters, anhydrides, wherein $R^2$ is as defined above, or
a partially or completely fluoro-substituted aromatic, for example, but not exhaustively $C_6F_6$, $C_{10}F_8$ (perfluoronaphthalene), 1-fluoro-2,4-dinitrobenzol (Sanger's reagent), 1-fluoro-4-nitrobenzol, 1-fluoro-2-nitrobenzol, in the presence of an auxiliary base B, which is at least as basic as the anion X,

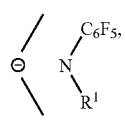
(I)

wherein $R^1$ is as defined above.

Reason: The reaction occurs with the highest yield according to the following stoichiometry:

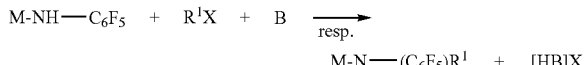
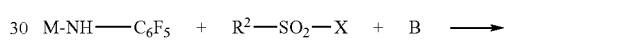

B can be: a neutral base, such as, for example, but not exhaustively, an alkyl amine $NH_{3-x}R^1_x$, guanidine or a saline base from the class of metalating agents (metal amide, metal hydride, metal alkyl, metal hydroxide, metal carbonate, metal (elemental)/metal preferably alkali metal or earth alkali metal), particularly preferable are strong and not particularly nucleophilic bases, e.g. $Na[N(SiMe_3)_2]$ or $K[O^tBu]$.

The reaction of trifluoromethylsulfonic acid anhydride with pentafluorophenyl aniline in the presence of 2 equivalents Na-bis-trimethylsilyl amide $Na[N(SiMe_3)_2]$ is named as an example of this:

In this, one equivalent pentafluorophenyl aniline is dissolved in THF, reacted at −80° C. with two equivalents $Na[N(SiMe_3)_2]$ and the reaction mixture is reacted with one equivalent of the electrophile (trifluoromethylsulfonic acid anhydride). The reaction provides the lithium salt of the anion I with $R^1=SO_2CF_3$; processing with aqueous HCl at a pH value of 2 to 5 provides the conjugate NH acid of this anion.

It is easily obvious to persons skilled in the art that other anions (I) according to the present invention can be produced in an analogous method. They can use the other anions according to the present invention with the help of their expertise and without leaving the scope of protection of the patent claims. The conjugate acids (X) can be obtained through protonation at a pH value of 0 to 6.

All of the R groups $R^1$ to $R^{25}$ listed in the disclosure at hand can stand—as stated—amongst others, for a linear or branched alkyl group with 1 to 20 C atoms. It must be emphasized that in all of these cases, such alkyl groups, which contain 1 to 4 C atoms, i.e. methyl, ethyl, n-propyl, isopropyl, n-butyl, 2-butyl and tert-butyl, are particularly preferable.

Ionic liquids according to the present invention are produced through reaction of the respective conjugate acids

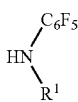

of the anion I

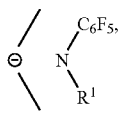

wherein
R¹ stands for a linear or branched, non-fluorinated, partially or completely fluorinated alkyl group with 1 to 20 C atoms, non-fluorinated, partially or completely fluorinated aryl group, a 2-nitroaryl group, a 4-nitroaryl group, a 2,4-dinitroaryl group, a non-fluorinated, partially or completely fluorinated benzyl group, or represents CN, CO—H, a CO-aryl group or a CO-alkyl group or
represents $R^1=-SO_2-R^2$, wherein
R₂ represents a linear or branched alkyl group with 1 to 20 C atoms or an aryl group or benzyl group and this alkyl group, benzyl group or aryl group is non-fluorinated, partially or completely fluorinated;
with a conjugate compound of the desired cation, namely
quaternary ammonium hydroxides, if a quaternary ammonium cation according to the above definition is desired as cation,
guanidinium ions according to the above definition (through ion exchange), if a quaternary guanidinium cation according to the above definition is desired as cation,
alkyl-alkylidene phosphoranes or aryl-alkylidene phosphoranes (P-ylides), if a phosphonium cation according to the above definition is desired as cation, or
one ketene N,N-diacetal, if a 2-alkyl-substituted imidazolium cation, imidazolidinium cation or benzimidazolium cation according to one of the above definitions is desired as cation,
a salt of an N-organo pyridinium according to the above definition, if a N-organo pyridinium cation is desired as cation,
in an organic solvent.

The solvent for the reaction is preferably chosen from the group of purely aliphatic, unsaturated and aromatic hydrocarbons, for example, toluol, partially or completely halogenated hydrocarbons (e.g. chlorobenzene, chloroform, tetrachlorocarbon, CFC, FC, frigenes), of the organic amines, ethers, alcohols (optionally mixed with water), ketones, DMF, DMSO, HMPT, of the organic carbonates, carboxylic acid amides and carboxylic acid esters and tetraalkylureas.

The technical state of the art knows of ionic liquids which contain quaternary 2-alkyl-substituted imidazolium cations, imidazolidinium cations or benzimidazolium cations. The disadvantage with the known methods for producing these ionic liquids is, however, that the ionic liquids can not be produced directly, quantitatively and anhydrously with their help.

Ketene N,N-diacetals are known to persons skilled in the art; they also know that these can be reprotonated to 2-alkyl-substituted imidazolium salts, imidazolidinium salts or benzimidazolium salts. Furthermore, it corresponds to the technical state of the art that nucleophilic carbenes can be protonated to the corresponding 2-H-substituted imidazolium salts, imidazolidinium salts or benzimidazolium salts.

It is, however, novel and surprising that the reaction of ketene N,N-diacetals with the conjugate acids $H[N(C_6F_5)R^1]$ of the anions $[N(C_6F_5)R^1]^-$ according to the present invention leads directly and quantitatively to the corresponding non-aqueous ionic liquids in an organic solvent. An example of this is shown below schematically for a 1,3-dialkyl-2-methylene imidazole as a representative of a ketene N,N-diacetal:

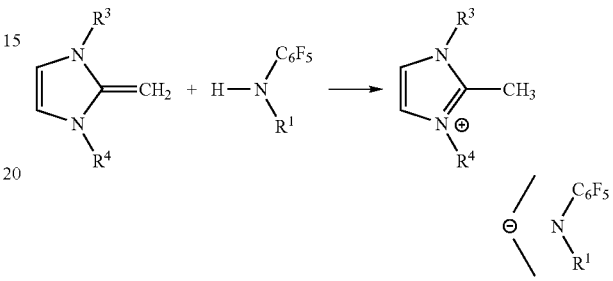

In this, $R^1$, $R^3$ and $R^4$ are as defined above. It is easily obvious to persons skilled in the art that this reaction is able to also be carried out, in an analogous method, with the corresponding 1,3-dialkyl-2-alkylene imidazolines, 1,3-diaryl-2-alkylene imidazolines, 1,3-dialkyl-2-alkylene benzimidazoles, 1,3-dialkyl-2-benzilidene imidazoles and further representatives of the class of ketene N,N-diacetals.

Likewise, the conjugate acids (X) of the anions (I) according to the present invention can be directly and quantitatively reacted to the corresponding ionic liquids with alkyl-alkylidene phosphoranes or aryl-alkylidene phosphoranes in an organic solvent. An example of this method is shown in embodiment 15 for producing methyltriphenylphosphonium-decafluorodiphenylamide and can also be used, without leaving the scope of protection of the patent claims, for producing other organophosphonium imide salts.

Furthermore, it is easily obvious to persons skilled in the art that the ketene N,N-diacetals can also be reacted to ionic liquids with other O—H—, C—H— and N—H—, halocarboxylic acids, as well as fluoroboric acids, fluorosilicic acids, fluorophosphoric acids, fluoroarsenic acids, fluoroantimonic acids, fluorosulfuric acids, furthermore all mineral acids and oxoacids of the non-metals and metals with a $pK_A$ value smaller than or equal to 15 measured in DMSO in an organic solvent.

Examples of acids to be named, but not exhaustively, are $HC(SO_2CF_3)_3$, $HN(SO_2CF_3)_2$, pentafluorophenol, $HBF_4$, $H_2SiF_6$, $HPF_6$, $HAsF_6$, $HSbF_6$, $HSO_3F$, HF, HCl, HBr, HI, as well as oxoacids, chosen from nitric acids, sulfuric acids, chloric acids, bromic acids, phosphoric acids, chromic acids, titanic acids and tungstic acids, vanadic acids, molybdic acids.

Persons skilled in the art can react the classes of protonic acids described above, with the help of their general expertise and without leaving the scope of protection of the patent claims, to 2-alkyl-imidazolium-based ionic liquids with ketene N,N-diacetals and to organophosphonium-based ionic liquids with alkyl-alkylidene phosphoranes or aryl-alkylidene phosphoranes.

2-alkyl-substituted quaternary imidazolium salts, imidazolidinium salts and benzimidazolium salts are particularly advantageous cations in ionic liquids, since they are less CH-acidic and, thus, more stable against a nucleophilic attack than the corresponding 2-H-imidazolium salts, which, as is known, are obtainable through carbenes.

The solvent for the reaction is chosen from the group of purely aliphatic, unsaturated or aromatic hydrocarbons, for example, toluol, partially or completely halogenated hydrocarbons (e.g. chlorobenzene, chloroform, tetrachlorocarbon, CFC, FC, frigenes), of the organic amines, ethers, alcohols (optionally mixed with water), ketones, DMF, DMSO, HMPT, of the organic carbonates, carboxylic acid amides and carboxylic acid esters and tetraalkylureas.

The ionic liquids according to the present invention can be used as a substitute for organic solvents in industrial syntheses. Through their low vapor pressure, reduction of gaseous emissions occurs. Processes, in which ionic liquids are used as a solvent, comprise a lower exposition potential for personnel involved, as well as a lower risk of explosion. Due to their exceptional solvent properties, ionic liquids are used as solvents for substances which are difficult to bring into solution with conventional organic solvents, such as e.g. cellulose.

Ionic liquids are, furthermore, suitable as extraction means, due to their solvent and absorption properties. They can thus be used in order to separate azeotropic mixtures. Moreover, they are used advantageously as mobile and/or stationary phases in chromatography, for example for GC, LC, HPLC, ion chromatography. Furthermore, ionic liquids with electrochemically inert, fluorinated anions are used as electrolyte systems for batteries, galvanic elements, fuel cells, and rechargeable battery packs (for example, lithium ion rechargeable batteries and lithium ion electrolytes).

They can also be used as heat transfer media in solar technical systems.

Some quaternary imidazolium salts are used as microbiocides. Several quaternary ammonium salts act as cationic surfactants.

EMBODIMENTS

1. 1-n-butyl-2,3-dimethyl-imidazolium Chloride

The product is known in literature, cf. V. Farmer, T. Welton, *Green Chemistry* 2002, 4, 97-102.

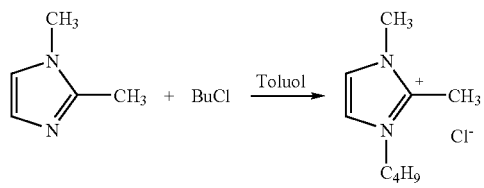

71.05 ml (0.680 mol) n-butylchloride is added to a solution of 59.43 g (0.618 mol) 1,2-dimethylimidazole in 50 ml toluol. The reaction mixture is heated for 24 h under reflux, wherein a two-phase system is formed. The mixture is stored for 8 h at −30° C., wherein a white solid is formed. The white solid obtained is recrystallized from warm acetonitrile. Yield: 70.00 g (60%) (white, hygroscopic solid).

$^1$H-NMR (CDCl$_3$, 200 MHz): δ=1.30 (s, 3H, NCH$_2$CH$_2$CH$_2$CH$_3$), 1.74 (sext, 2 H, NCH$_2$CH$_2$CH$_2$CH$_3$), 2.16 (quint, 2 H, NCH$_2$CH$_2$CH$_2$CH$_3$), 3.20 (s, 3 H, NCH$_3$), 4.42 (s, 3 H, CCH$_3$), 4.62 (t, 2 H, NCH$_2$CH$_2$CH$_2$CH$_3$), 8.01 (d, 1 H, BuNCH), 8.25 (d, 1 H, (MeNCH).

2. 1-n-butyl-3-methyl-2-methylene imidazoline

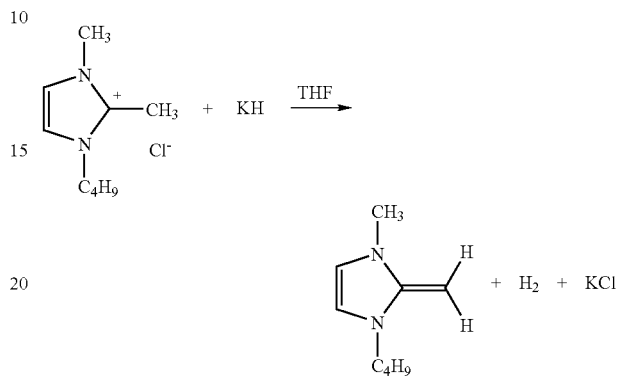

9.43 g (49.60 mmol) 1-n-butyl-2,3-dimethyl-imidazolium chloride and 4.97 g (123.91 mmol) KH are mixed in a 250 ml flask in a glove box. 100 ml THF is added to the solution, and this is stirred for 60 h at room temperature. The reaction mixture obtained is filtrated over celite, and all components which are volatile at room temperature are condensed from the solution. Subsequently, the product is distilled at 160° C./0.1 mbar in a Schlenk tube cooled with nitrogen. Yield: approx. 70% (colorless liquid extremely sensitive to humidity, which quickly colors yellow under partial decomposition at room temperature).

$^1$H-NMR (C$_6$D$_6$, 300 MHz): δ=0.92 (t, 3 H, NCH$_2$CH$_2$CH$_2$CH$_3$), 1.30 (sext, 2 H, NCH$_2$CH$_2$CH$_2$CH$_3$), 1.60 (quint, 2 H, NCH$_2$CH$_2$CH$_2$CH$_3$), 2.75 (s, 3 H, NCH$_3$), 2.77 (s, 1 H, CCH$_2$), 2.83 (s, 1 H, CCH$_2$), 3.22 (t, 2 H, NCH$_2$CH$_2$CH$_2$CH$_3$), 5.75 (s, 1 H, BuNCH), 5.80 (s, 1 H, MeNCH).

$^{13}$C-NMR (C$_6$D$_6$, 50 MHz): δ=13.88 (NCH$_2$CH$_2$CH$_2$CH$_3$), 20.21 (NCH$_2$CH$_2$CH$_2$CH$_3$), 29.65 (NCH$_2$CH$_2$CH$_2$CH$_3$), 32.52 (NCH$_3$), 39.84 (CCH$_2$), 45.80 (NCH$_2$CH$_2$CH$_2$CH$_3$), 112.07 (BuNCH), 113.06 (MeNCH), 151.98 (NCN)

3. 1-ethyl-3-methyl-2-methylene imidazoline

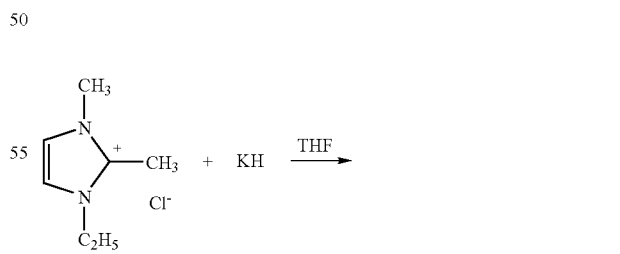

5.96 g (37.12 mmol) 1-ethyl-2,3-dimethyl-imidazolium chloride and 2.98 g (74.24 mmol) KH are mixed in a 250 ml flask in a glove box. 100 ml THF is added to the solution, and this is stirred for 60 h at room temperature. The reaction mixture obtained is filtrated over celite, and all components which are volatile at room temperature are condensed from the solution. Subsequently, the product is distilled at 160° C./0.1 mbar in a Schlenk tube cooled with nitrogen. Yield: approx. 70% (colorless liquid extremely sensitive to humidity, which quickly colors yellow under partial decomposition at room temperature).

$^1$H-NMR ($C_6D_6$, 200 MHz): δ=0.92 (t, 3 H, $NCH_2CH_3$), 2.56 (s, 3 H, $NCH_3$), 2.65 (s, 2 H, $CCH_2$), 3.00 (q, 2 H, $NCH_2CH_3$), 5.56 (d, 1 H, EtNCH), 5.61 (d, 1 H, MeNCH).

$^{13}$C-NMR ($C_6D_6$, 50 MHz): δ=12.64 ($NCH_2CH_3$), 32.49 ($CCH_2$), 39.82 ($NCH_3$), 40.42 ($NCH_2CH_3$), 110.94 (EtNCH), 113.27 (MeNCH), 151.80 (NCN).

4. 1,3-di(iso-propyl)imidazolium-pentafluorophenolate

The N-heterocyclic carbene, as well as the method for producing 2-H-imidazole-based ionic liquids, are known from WO 01/77081 A1.

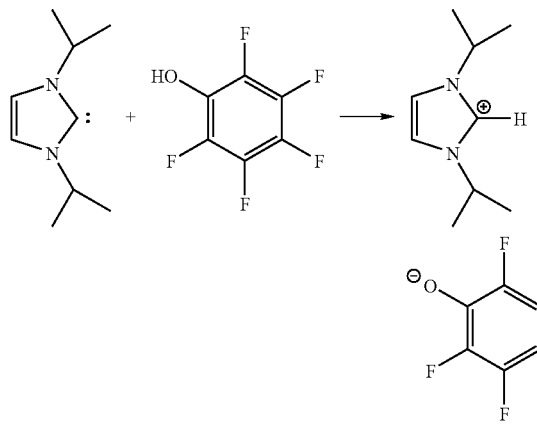

1.25 ml (8.15 mmol) 1,3-di(iso-propyl)imidazole-2-ylide is added to a solution of 1.50 g (8.15 mmol) pentafluorophenol in diethylether cooled to −78° C. by means of a syringe. The reaction mixture is warmed to room temperature over a period of 5 h and stirred for 8 h at room temperature. Subsequently, all volatile components are removed in vacuum; the residue is washed with 20 ml hexane and subsequently dried in vacuum. The desired product is obtained as a white solid, which can be recrystallized from dichloromethane at −30° C.

$^1$H-NMR ($D_3$CCN, 300 MHz): δ=1.50 (d, 12 H, $NCH(CH_3)_2$), 4.60 (sept, 2 H, NCH), 7.50 (s, 2 H, NCHCHN), 9.40 (s, 1 H, NCHN).

$^{13}$C-NMR ($D_3$CCN, 50 MHz): 22.79 ppm ($NCH(CH_3)_2$), 53.98 ppm ($NCH(CH_3)_2$), 121.31 ppm (NCHCHN), 135.11 ppm (NCN).

$^{19}$F-NMR ($D_3$CCN, 282 MHz): δ=−197.11 (t, 1 F, p-F), −174.06 (2 F, m-F), −173.99 (2 F, o-F).

5. 1,3-di(iso-propyl)imidazolium-decafluorodiphenyl imide

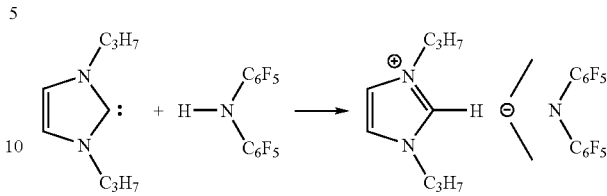

0.2 ml (1.31 mmol) 1,3-di(iso-propyl)imidazole-2-ylide is added under stirring to a solution of 0.524 g (2.86 mmol) decafluorodiphenyl amine 5 ml $Et_2O$ in a Schlenk flask at −78° C. The mixture is brought to room temperature within 19 h, and the solvent is removed in vacuum. The residue is digested with 10 ml n-hexane, filtrated, washed with 10 ml n-pentane and dried in vacuum. 0.530 mg (1.06 mmol, 80.9%) di(iso-propyl)imidazolium-decafluorodiphenyl imide is obtained in the form of a light yellow solid. Colorless crystals, which are suitable for determining the x-ray structure, are obtained through recrystallization from 10 ml $Et_2O$ at −30° C.

mp: 109° C.

Mass spectrum (EI):

m/z=43 (27.72, i-Pr+), 110 (12.51, $lm^{iPr}$-H-i-Pr), 152 (11.13, $lm^{iPr}$H+), 349 (28.42, $(C_6F_5)_2NH^+$)

C, H, N analysis: found (calculated)

C, 50.14% (50.31%), H, 3.43% (3.42%), N, 8.72% (8.38%)

IR: $cm^{-1}$: 30.46 s, 2723.66 s, 2362.95 s, 1618.38 s, 1305.89 s, 1263.45 s, 1018.48 m, 968.33 m,
939.39 s, 814.01 s, 740.71 s, 557.46 m $^1$H-NMR ($D_3$CCN, 300 MHz): δ=0.83 ppm (d, 12 H, $NCH(CH_3)_2$), 3.90 ppm (sept, 2 H, NCH), 5.85 ppm (s, 2 H, NCHCHN), 9.40 (s, 1 H, NCHN).

$^{13}$C-NMR ($D_3$CCN, 50 MHz): 21.96 ppm ($NCH(CH_3)_2$), 52.79 ppm ($NCH(CH_3)_2$), 118.40 ppm (NCHCHN), 137.98 ppm (NCN).

$^{19}$F-NMR ($D_3$CCN, 282 MHz): δ=−183.35 ppm (t, 1 F, p-F), −169.80 ppm (2 F, m-F), −160.94 ppm (d, 1 F, o-F).

X-Ray Structure Analysis:

Mo-Kα radiation (wavelength: 71.069 nm), 20° C.

stoichiometric formula: $C_{21}H_{17}F_{10}N_3$ molar mass: 501.38 g/mol number of formula units: 4 unit cell: a=14.1670 (16) Å, b=11.0290 (10) Å, c=13.6160 (14) Å

α=90.00°, β=91.0680 (10)° crystal system: monoclinic space group: C2/c

X-ray density: 1.566 g/ml absorption coefficient: 0.155 $mm_{-1}$

Mp: 109° C.

measured reflections: 10551 observed reflections: 1626 number of independent reflexes: 2269 measurement range (θ): 2.34-26.76° parameter count: 190

$R_1$; $R_2$: 0.0351; 0.0934 residual electron density (min., max.): −0.235, 0.211

$^{13}$C-NMR ($D_3$CCN, 50 MHz): δ=10.07 ($NCH_2CH_2CH_2CH_3$), 13.78 ($NCH_2CH_2CH_3$), 20.12 ($CCH_3$), 32.33 ($NCH_3$), 35.72 ($NCH_2CH_2CH_2CH_3$), 48.97

(NCH$_2$CH$_2$CH$_2$CH$_3$), 121.92 (BuNCH), 123.38 (MeNCH), 121.70 (q, COO), 145.42 (NCN), 160.27 (q, CF$_3$).

$^{19}$F-NMR (D$_3$CCN, 282 MHz): δ=−75.58 (s, 3 F, OOCCF$_3$).

6. 1-n-butyl-2,3-dimethylimidazolium-trifluoroacetate

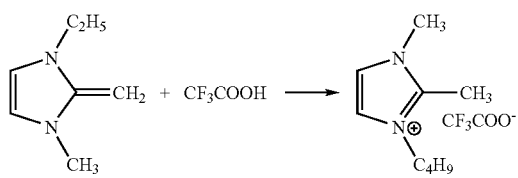

1.84 ml (12.09 mmol) 1-n-butyl-3-methyl-2-methylene imidazoline is added to a solution of 1.38 g (12.09 mmol) trifluoroacetic acid in diethylether cooled to −78° C. by means of a syringe. The reaction mixture is slowly warmed to room temperature, wherein a white solid is formed and is stirred overnight at room temperature. Subsequently, all volatile components are removed in vacuum; the residue is washed with 20 ml hexane and, subsequently dried in vacuum. The desired product is obtained as a white solid, which can be recrystallized from dichloromethane.

$^1$H-NMR (D$_3$CCN, 300 MHz): δ=0.92 (t, 3 H, NCH$_2$CH$_2$CH$_2$CH$_3$), 1.33 (sext, 2 H, NCH$_2$CH$_2$CH$_2$CH$_3$), 1.72 (quint, 2 H, NCH$_2$CH$_2$CH$_2$CH$_3$), 2.51 (s, 3 H, NCH$_3$), 3.71 (s, 3 H, CCH$_3$), 4.04 (t, 2 H, NCH$_2$CH$_2$CH$_2$CH$_3$), 7.23 (d, 1 H, BuNCH), 7.47 (d, 1 H, MeNCH).

$^{13}$C-NMR (D$_3$CCN, 50 MHz): δ=10.07 (NCH$_2$CH$_2$CH$_2$CH$_3$), 13.78 (NCH$_2$CH$_2$CH$_2$CH$_3$), 20.12 (CCH$_3$), 32.33 (NCH$_3$), 35.72 (NCH$_2$CH$_2$CH$_2$CH$_3$), 48.97 (NCH$_2$CH$_2$CH$_2$CH$_3$), 121.92 (BuNCH), 123.38 (MeNCH), 121.70 (q, COO), 145.42 (NCN), 160.27 (q, CF$_3$).

$^{19}$F-NMR (D$_3$CCN, 282 MHz): δ=−75.58 (s, 3 F, OOCCF$_3$).

7. 1-n-butyl-2,3-dimethylimidazolium-decafluorodiphenyl imide

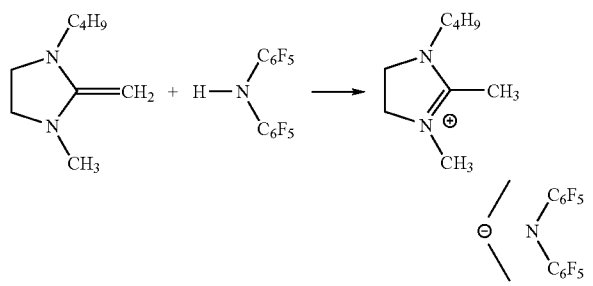

1.96 ml (12.85 mmol) 1-n-butyl-3-methyl-2-methylene imidazoline is added to a solution of 4.49 g (12.85 mmol) decafluorodiphenyl amine in diethylether cooled to −78° C. by means of a syringe. The reaction mixture is warmed to room temperature over a period of 5 h and stirred for 8 h at room temperature, wherein a dark brown solution is formed. Subsequently, all volatile components are removed in vacuum; the residue is washed with 20 ml pentane and, subsequently, dried in vacuum. The desired product is obtained as brown oil.

$^1$H-NMR (C$_6$D$_6$, 300 MHz): δ=0.73 (t, 3 H, NCH$_2$CH$_2$CH$_2$CH$_3$), 0.89 (sext, 2 H, NCH$_2$CH$_2$CH$_2$CH$_3$), 1.14 (quint, 2 H, NCH$_2$CH$_2$CH$_2$CH$_3$), 1.59 (s, 3 H, NCH$_3$), 2.86 (s, 3 H, CCH$_3$), 3.19 (t, 2 H, NCH$_2$CH$_2$CH$_2$CH$_3$), 6.63 (s, 1 H, BuNCH), 6.67 (s, 1 H, MeNCH).

$^{13}$C-NMR (C$_6$D$_6$, 50 MHz): δ=7.87 (NCH$_2$CH$_2$CH$_2$CH$_3$), 13.10 (NCH$_2$CH$_2$CH$_2$CH$_3$), 19.46 (CCH$_3$), 31.32 (NCH$_3$), 33.91 (NCH$_2$CH$_2$CH$_2$CH$_3$), 47.97 (NCH$_2$CH$_2$CH$_2$CH$_3$), 120.66 (BuNCH), 122.27 (MeNCH), 142.84 (NCN), 130.83-140.5 (m, C(Ar$^F$)).

$^{19}$F-NMR (C$_6$D$_6$, 282 MHz): δ=−185.64 (m, 2 F, p-F), −170.45 (t, 4 F, o-F), −161.12 (dd, 4 F, m-F).

X-Ray Structure Analysis:
Mo-Kα radiation (wavelength: 71.069 nm), 20° C.
stoichiometric formula: C$_{21}$H$_{17}$F$_{10}$N$_3$
molar mass: 501.38 g/mol
number of formula units: 2
unit cell: a=9.8625 (11) Å, b=10.3192 (12) Å, c=10.8965 (12) Å
α=81.843 (13)°, β=80.651 (13)°, γ=75.228 (13)°
crystal system: triclinic
space group: P$\bar{1}$
radiographic density: 1.583 g/ml
absorption coefficient: 0.157 mm$^{-1}$
Mp: 109° C.
measured reflections: 10424
reflections used: 8000
number of independent reflections: 3839
measurement area (O): 2.05-26.01°
parameter count: 375
R$_1$; R$_2$: 0.0337; 0.0914
residual electron density (min., max.): −0.158, 0.193

8. 1-ethyl-2,3-dimethylimidazolium-pentafluorophenolate

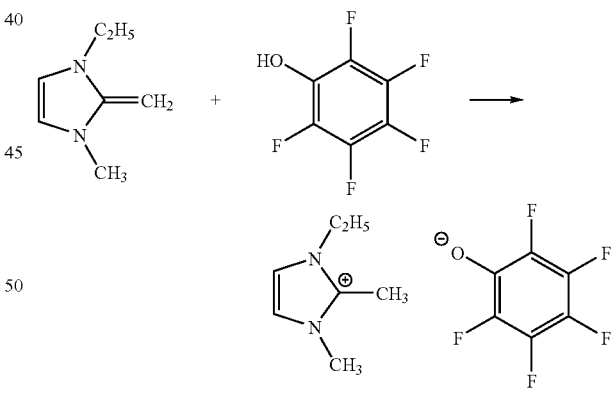

1.48 ml (11.95 mmol) 1-ethyl-3-methyl-2-methylene imidazoline is added to a solution of 2.20 g (11.95 mmol) pentafluorophenol in diethylether cooled to −78° C. by means of a syringe. The reaction mixture is warmed to room temperature over a period of 5 h and stirred at room temperature for 8 h. The precipitated, colorless solid is filtered off, washed twice with 20 ml diethylether and, subsequently, dried in vacuum. The desired product is obtained as a colorless solid which melts at 144° C.

$^1$H-NMR (D$_3$CCN, 300 MHz): δ=1.3/(t, 3 H, NCH$_2$CH$_3$), 2.50 (s, 3 H, NCH$_3$), 3.70 (s, 3 H, CCH$_3$), 4.08 (q, 2 H, NCH$_2$CH$_3$), 7.33 (d, 1 H, EtNCH), 7.35 (d, 1 H, MeNCH).

$^{13}$C-NMR (D$_3$CCN, 75 MHz): δ=9.90 (NCH$_2$CH$_3$), 15.16 (CCH$_3$), 35.63 (NCH$_3$), 44.37 (NCH$_2$CH$_3$), 121.28 (EtNCH), 123.42 (MeNCH), 145.22 (NCN).

$^{19}$F-NMR (D$_3$CCN, 282 MHz): δ=−197.97 (br, 1 F, p-F), 174.40-174.12 (m, 4 F, o-F+m-F).

C, H, N analysis: found (calculated)

C, 50.19% (50.65%), H, 4.59% (4.22%), N, 9.08% (9.09%)

9. 1-ethyl-2,3-dimethylimidazolium-decafluorodiphenyl imide

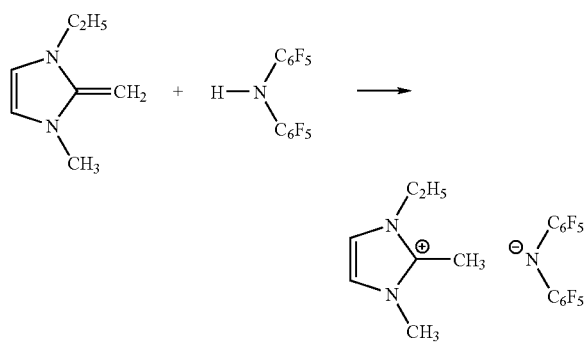

0.28 ml (2.29 mmol) 1-ethyl-3-methyl-2-methylene imidazoline is added to a solution of 0.80 g (2.29 mmol) decafluorodiphenyl amine in diethylether cooled to −78° C. by means of a syringe. The reaction mixture is warmed to room temperature over a period of 5 h and stirred at room temperature for 8 h. The precipitated, light yellow solid is filtered off, washed twice with 20 ml diethylether and, subsequently, dried in vacuum. The desired product is obtained as a colorless solid, which melts at 98° C.

$^1$H-NMR (D$_3$CCN, 300 MHz): δ=1.37 (t, 3 H, NCH$_2$CH$_3$), 2.47 (s, 3 H, NCH$_3$), 3.68 (s, 3 H, CCH$_3$), 4.06 (q, 2 H, NCH$_2$CH$_3$), 7.24 (d, 1 H, EtNCH), 7.27 (d, 1 H, MeNCH).

$^{13}$C-NMR (D$_3$CCN, 75 MHz): δ=9.92 (NCH$_2$CH$_3$), 15.14 (CCH$_3$), 35.68 (NCH$_3$), 44.42 (NCH$_2$CH$_3$), 121.22 (EtNCH), 123.35 (MeNCH), 145.26 (NCN).

$^{19}$F-NMR (D$_3$CCN, 282 MHz): δ=−187.66 (m, 2 F, p-F), −172.16 (t, 4 F, o-F), −162.86 (dd, 4 F, m-F).

C, H, N analysis: found (calculated)

C, 47.59% (48.20%), H, 2.75% (3.42%), N, 8.96% (8.88%)

10. 1-n-butyl-2,3-dimethylimidazolium-pentafluorophenyl-nonafluorobutylsulfonyl imide

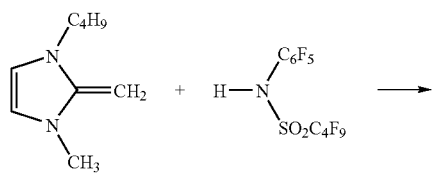

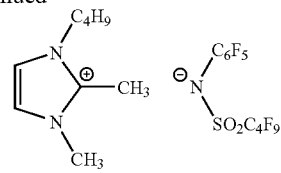

0.51 ml (3.37 mmol) 1-n-butyl-3-methyl-2-methylene imidazoline is added by means of a syringe to a solution of 1.57 g (3.37 mmol) pentafluorophenyl-nonafluorobutylsulfonyl amine in diethylether cooled to −78° C. The reaction mixture is warmed to room temperature over a period of 5 h and stirred at room temperature for 8 h. Subsequently, all volatile components are removed in vacuum, and the desired product is obtained as brown oil.

$^1$H-NMR (D$_3$CCN, 300 MHz): δ=0.92 (t, 3 H, NCH$_2$CH$_2$CH$_2$CH$_3$), 1.32 (sext, 2 H, NCH$_2$CH$_2$CH$_2$CH$_3$), 1.72 (quint, 2 H, NCH$_2$CH$_2$CH$_2$CH$_3$), 2.50 (s, 3 H, NCH$_3$), 3.69 (s, 3 H, CCH$_3$), 4.02 (t, 2 H, NCH$_2$CH$_2$CH$_2$CH$_3$), 7.25 (s, 1 H, BuNCH), 7.27 (s, 1 H, MeNCH).

$^{13}$C-NMR (D$_3$CCN, 75 MHz): δ=8.78 (NCH$_2$CH$_2$CH$_2$CH$_3$), 12.42 (NCH$_2$CH$_2$CH$_2$CH$_3$), 18.84 (CCH$_3$), 31.03 (NCH$_3$), 34.45 (NCH$_2$CH$_2$CH$_2$CH$_3$), 47.74 (NCH$_2$CH$_2$CH$_2$CH$_3$), 120.53 (BuNCH), 121.99 (MeNCH), 144.80 (NCN), 118.83-123.55 (m, C(Alk$^F$)). 133.86-144.92 (m, C(Ar$^F$)).

$^{19}$F-NMR (D$_3$CCN, 188 MHz): δ=−165.17 (m, 1 F, p-F), −163.79 (t, 2 F, m-F), −146.56 (d, 4 F, m-F), −121.82 (2 F, CF$_2$SO$_2$), −116.74 (2 F, CF$_2$CF$_2$SO$_2$), −109.97 (2 F, CF$_2$CF$_3$), −76.88 (3 F, CF$_3$).

11. Pentafluorophenyl-nonafluorobutylsulfonyl imine

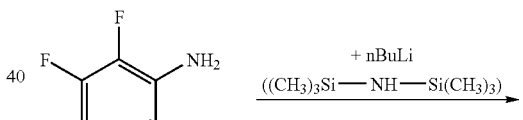

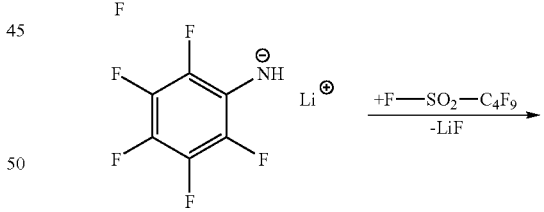

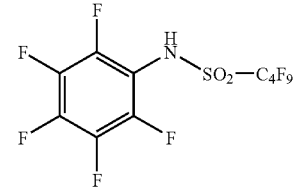

Initially, 66.74 ml of a 1.6-molar solution of n-butyl lithium in hexane (corresponds to 106.78 mmol) is added to a solution of 22.27 ml (106.78 mmol) hexamethyldisilazane in 50 ml THF cooled to −78° C. The solution is warmed to room temperature and stirred for 1 h at this temperature. Subsequently, it is cooled again to −78° C. and a solution of 7.82 g (42.71 mmol) pentafluoro-aniline in 100 ml THF is added.

The reaction mixture is brought to a temperature of 0° C. and kept at this temperature for 2 h. It is cooled again to −78° C. and 7.67 ml nonafluorobutylsulfonylfluoride is added by means of a syringe. The reaction mixture is brought to room temperature over a period of 8 h and, subsequently, stirred for 2 days at room temperature. Subsequently, 200 ml of water is added and the aqueous phase is brought to a pH value of 6 by means of half-concentrated HCl. The mixture is extracted three times with 100 ml diethylether, the combined organic phases are dried over sodium sulfate, and, subsequently, all volatile compounds are removed on a rotary evaporator. The crude product obtained is recrystallized in boiling toluol. A beige powder is obtained.

$^{19}$F-NMR (D$_3$CCN, 188 MHz): δ=−169.40 (m, 1 F, p-F), −168.53 (t, 2 F, m-F), −151.21 (d, 2 F, m-F), −126.62 (2 F, CF$_2$SO$_2$), −121.56 (2 F, CF$_2$CF$_2$SO$_2$), −114.74 (2 F, CF$_2$CF$_3$), −81.70 (3 F, CF$_3$).

12. 1-n-butyl-3-methylimidazolium-pentafluorophenyl-nonafluorobutylsulfonyl imide

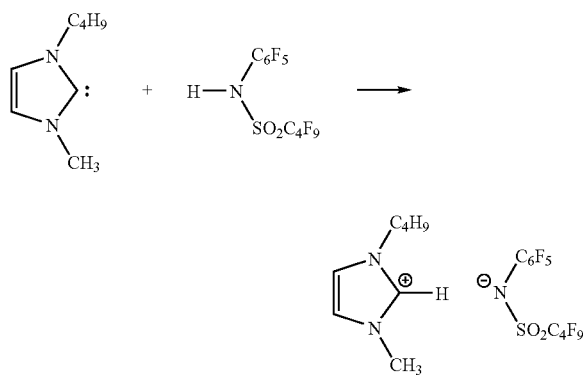

0.51 ml (3.37 mmol) 1-n-butyl-3-methyl-imidazole-2-ylide is added by means of a syringe to a solution of 1.34 g (2.877 mmol). pentafluorophenyl-nonafluorobutylsulfonyl amine in diethylether cooled to −78° C. The reaction mixture is warmed to room temperature over a period of 5 h and stirred at room temperature for 8 h. Subsequently, all volatile components are removed in vacuum, and the desired product is obtained as brown oil.

$^1$H-NMR (D$_3$CCN, 300 MHz): δ=0.93 (t, 3 H, NCH$_2$CH$_2$CH$_2$CH$_3$), 1.31 (sext, 2 H, NCH$_2$CH$_2$CH$_2$CH$_3$), 1.78 (quint, 2 H, NCH$_2$CH$_2$CH$_2$CH$_3$), 3.81 (s, 3 H, NCH$_3$), 4.11 (t, 2 H, NCH$_2$CH$_2$CH$_2$CH$_3$), 7.33 (s, 1 H, BuNCH), 7.36 (s, 1 H, MeNCH), 8.44 (s, 1 H, N$_2$CH).

$^{13}$C-NMR (D$_3$CCN, 75 MHz): δ=13.63 (NCH$_2$CH$_2$CH$_2$CH$_3$), 19.98 (NCH$_2$CH$_2$CH$_2$CH$_3$), 32.61 (NCH$_2$CH$_2$CH$_2$CH$_3$), 36.86 (NCH$_3$), 50.32 (NCH$_2$CH$_2$CH$_2$CH$_3$), 123.32 (BuNCH), 124.68 (MeNCH), 137.00 (NCN).

$^{19}$F-NMR (D$_3$CCN, 188 MHz): δ=−165.28 (m, 1 F, p-F), −163.82 (t, 2 F, m-F), −146.64 (d, 2 F, m-F), −121.76 (2 F, CF$_2$SO$_2$), −116.72 (2 F, CF$_2$CF$_2$SO$_2$), −109.99 (2 F, CF$_2$CF$_3$), −76.85 (3 F, CF$_3$).

13. 1-n-butyl-3-methylimidazolium-decafluorodiphenyl imide

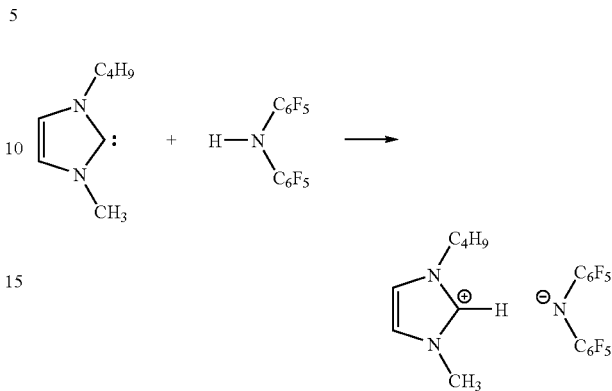

0.31 ml (2.52 mmol) 1-n-butyl-3-methyl-imidazole-2-ylide is added by means of a syringe to a solution of 0.88 g (2.52 mmol) decafluorodiphenyl amine in diethylether cooled to −78° C. The reaction mixture is warmed to room temperature over a period of 5 h and stirred at room temperature for 8 h. Subsequently, all volatile components are removed in vacuum, and the desired product is obtained as brown oil.

$^1$H-NMR (D$_3$CCN, 300 MHz): δ=0.88 (t, 3H, NCH$_2$CH$_2$CH$_2$CH$_3$), 1.27 (sext, 2H, NCH$_2$CH$_2$CH$_2$CH$_3$), 1.75 (quint, 2H, NCH$_2$CH$_2$CH$_2$CH$_3$), 3.80 (s, 3H, NCH$_3$), 4.09 (t, 2H, NCH$_2$CH$_2$CH$_2$CH$_3$), 7.34 (s, 1H, BuNCH), 7.39 (s, 1H, MeNCH), 8.87 (s, 1 H, N$_2$CH).

$^{13}$C-NMR (D$_3$CCN, 75 MHz): δ=13.63 (NCH$_2$CH$_2$CH$_2$CH$_3$), 20.07 (NCH$_2$CH$_2$CH$_2$CH$_3$), 32.69 (NCH$_2$CH$_2$CH$_2$CH$_3$), 36.78 (NCH$_3$), 50.38 (NCH$_2$CH$_2$CH$_2$CH$_3$), 123.34 (BuNCH), 124.69 (MeNCH), 137.60 (NCN), 131.92-143.18 (m, C(Ar$^F$)).

$^{19}$F-NMR (D$_3$CCN, 282 MHz): δ=−186.18 ppm (t, 1 F, p-F), −171.60 ppm (2 F, m-F), −162.22 ppm (d, 1 F, o-F).

14. Illustration of nBu$_4$N[N(C$_6$F$_5$)$_2$]

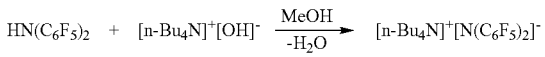

1.15 ml of tetra-n-butylammonium hydroxide solution (Aldrich; 1 M, 1.15 mmol) in methanol is added at RT to a solution of 0.40 g (1.15 mmol) DFDPA-H in 5 ml methanol. The reaction mixture is stirred at RT for 2 h. The solvent is removed in vacuum; the residue is recrystallized from diethylether and dried in vacuum. White needles. Yield 0.55 g (81%).

Mp. 97.6° C.

C$_{28}$H$_{36}$F$_{10}$N$_2$O (590.58 g/mol). Calc. (found) C 56.94 (56.92); N 4.74 (5.11); H 6.14 (6.67).

$^1$H-NMR (400.0 MHz, THF-d$_8$): δ=0.95 (t, 3H, CH$_3$, $^3J_{H\text{-}H}$=7.36 Hz), 1.30-1.40 (m, 2H, CH$_2$), 1.62-1.70 (m, 2H, CH$_2$), 3.21-3.25 (m, 2H, CH$_2$) ppm.

$^{13}$C-NMR (125.7 MHz, THF-d$_8$): δ=13.7 (s, CH$_3$), 20.4 (s, CH$_2$), 24.4 (s, CH$_2$), 59.2 (s, NCH$_2$), 129.2 (dm, $^1J_{C\text{-}F}$=231.3 Hz, C$_6$F$_5$), 134.4 (t, $^2J_{C\text{-}F}$=12.1 Hz, C$_6$F$_5$), 138.8 (dm, $^1J^{C\text{-}F}$=241.1 Hz, C$_6$F$_5$), 141.3 (dm, $^1J_{C\text{-}F}$=233.8 Hz, C$_6$F$_5$) ppm.

$^{19}$F-NMR (188.2 MHz, THF-d$_8$): δ=−183.6 (m, 1F, CF$_{para}$), −167.5 (t, $^3J_{F-F}$=20 Hz, 2F, CF$_{meta}$), −156.8 (m, 2F, CF$_{ortho}$) ppm.

IR (Nujol): $\tilde{v}$=2726 w, 2602 w, 1635 w, 1510 m, 1480 s, 1465 s, 1379 m, 1307 m, 1261 w, 1195 w, 1024 s, 995 s, 966 m, 706 m, 644 m, 559 m, 424 w cm$^{-1}$.

Crystal structure analysis of Bu$_4$N [N(C$_6$F$_5$)$_2$]

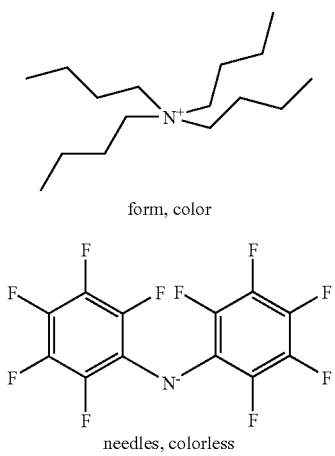

form, color needles, colorless

| | |
|---|---|
| crystal size | 0.30 × 0.10 × 0.06 mm³ |
| crystal system | triclinic |
| space group | P$\bar{1}$    Z = 2 |
| unit cell | a = 8.6597(12) Å   α = 75.023(11)°. |
| | b = 12.0615(16) Å   β = 88.185(11)°. |
| | c = 14.383(2) Å   γ = 74.643(10)°. |
| volume | 1398.4(3) Å³ |
| unit cell determination | 10121 Reflexionen |
| empirical formula | C$_{28}$H$_{36}$F$_{10}$N$_2$ |
| molecular weight | 590.59 |
| density (calculated) | 1.403 Mg/m³ |
| absorption coefficient | 0.129 mm$^{-1}$ |
| F(000) | 616 |
| diffractometer type | IPDS2 |
| wavelength | 0.71073 Å |
| temperature | 193(2) K |
| theta range for data collection | 1.47 to 26.23°. |
| index ranges | −10 <= h <= 10, −14 <= k <=14, |
| | −17 <= l <= 17 |
| data collection software | STOE Win-Xpose (X-Area) |
| cell refinement software | STOE Win-Cell (X-Area) |
| data reduction software | STOE Win-Integrate (X-Area) |
| collected reflections | 18043 |
| independent reflections | 5590 [R(int) = 0.0544] |
| correlation with theta = 26.23° | 99.4% |
| observed reflexes | 3269[l > 2sigma(l)] |
| reflexes used for fine adjustment | 5590 |
| extinction coefficient | X = 0.0160(16) |
| absorption correction | None |
| max. and min. transmission | 0.9923 and 0.9625 |
| largest diffraction peak and volume | 0.189 and −0.172 e.Å$^{-3}$ |
| resolution | direct methods |
| refinement | full-matrix least-squares on F² |
| hydrogen atoms | calculated positions, |
| | U(H) = 1.2(1.5)*Ueq(C) |
| U(H) = 1.2(1.5)*Ueq(C) | |
| programs used | SHELXS-97 (Sheldrick, 1997) |
| | SHELXL-97 (Sheldrick, 1997) |
| | DIAMOND 2.1, STOE IPDS software |
| data/limitations/parameter | 5590/0/366 |
| test of goodness of fit for F² | 0.875 |
| R index (all data) | wR2 = 0.0976 |
| R index conventional [l > 2sigma(l)] | R1 = 0.0396 |

15. Methyltriphenylphosphonium-decafluorodiphenyl imide

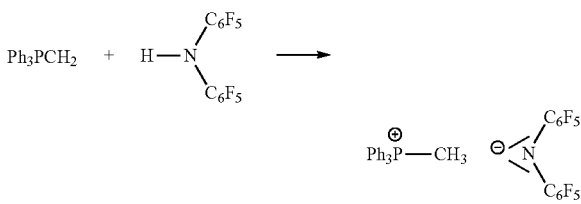

A solution of 0.79 g (2.87 mmol) triphenylphosphonium methylide in 10 ml toluol is added to a solution of 1.00 g (2.87 mmol) decafluorodiphenyl amine in 20 ml toluol at room temperature. A colorless precipitate is formed immediately. The reaction mixture is stirred at room temperature for 1 h and, subsequently, filtered off over a reverse frit. The solid obtained is washed with 20 ml hexane and dried in vacuum. The desired product is obtained as a colorless solid.

$^1$H-NMR (D$_3$CCN, 200 MHz): δ=2.81 (d, 2 H, PCH$_3$), 7.60-7.90 (m, 15 H, Ar—H).

$^{13}$C-NMR (D$_3$CCN, 50 MHz): δ=9.28 (d, PCH$_3$), 120.37 (d, i-C), 131.15 (d, o-C), 134.24 (d, m-C), 136.08 (d, p-C).

$^{19}$F-NMR (D$_3$CCN, 188 MHz): δ=−182.48 (t, 2 F, p-F), −167.12 (4 F, m-F), −157.77 (d, 4 F, o-F).

$^{31}$P-NMR (D$_3$CCN, 81 MHz): δ=31.37 (Ph$_3$PCH$_3$).

Figure Legends and List of Reference Numerals

Figure 2:
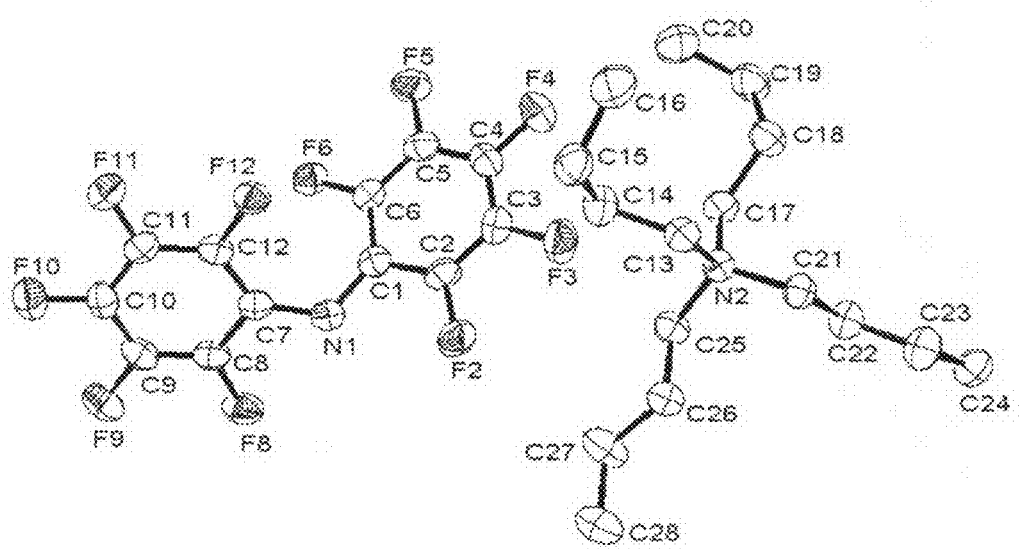

FIG. 1: structure model of 1,3-di(isopropyl)imidazolium-decafluorodiphenyl amide FIG. 2: structure model of Bu$_4$N[N(C$_6$F$_5$)$_2$]

Figure 3:
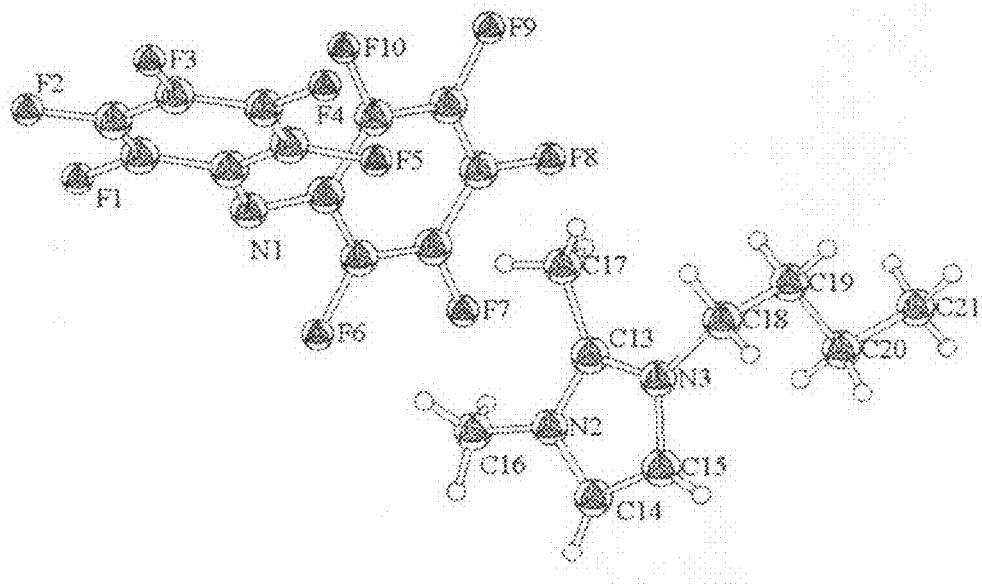

FIG. 3: structure model of 1-n-butyl-2,3-dimethylimidazolium-decafluoro-diphenyl amide

The invention claimed is:

1. Salt comprising
   a) an anion of the general formula

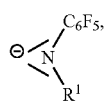 (I)

wherein
R$^1$=—SO$_2$—R$^2$, wherein R$^2$ represents a branched or unbranched alkyl group with 1 to 20 C atoms or an aryl group or benzyl group and this alkyl group, benzyl group, or aryl group is non-fluorinated, partially or completely fluorinated, wherein R$^2$ is not CF$_3$; and
   b) a cation, wherein said cation is chosen from the group of phosphonium ions, guanidinium ions, imidazolium ions, imidazolidinium ions, benzimidazolium ions and N-organo-pyridinium ions.

2. Salt according to claim 1, wherein the cation is a phosphonium ion of the general formula

[PR$^3$R$^4$R$^5$R$^7$]$^+$ (III), wherein R$^3$, R$^4$ and R$^5$ represent, independently from one another, a linear or branched alkyl group with 1 to 20 C atoms or an aryl group or a benzyl group, and $R^7$ represents a linear or branched alkyl group with 1 to 20 C atoms or an aryl group or a benzyl group.

3. Salt according to claim 1, wherein the cation is a guanidinium ion of the general formula

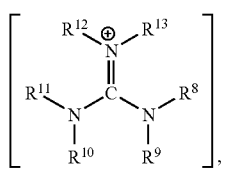
(IV)

wherein
$R^8$, $R^9$, $R^{10}$, $R^{11}$, $R^{12}$ and $R^{13}$ represent, independently from one another, an H atom, or a linear or branched alkyl group with 1 to 20 C atoms or an aryl group.

4. Salt according to claim 1, wherein the cation is an imidazolium ion of the general formula

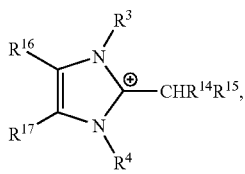
(V)

wherein
$R^3$ and $R^4$ are as defined above and
$R^{14}$, $R^{15}$, $R^{16}$ and $R^{17}$ stand, independently from one another, respectively, for an H atom, a branched or unbranched alkyl group with 1 to 20 C atoms, an aryl or a benzyl group.

5. Salt according to claim 1, wherein the cation is an imidazolidinium ion of the general formula

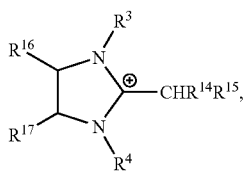
(VI)

wherein $R^3$, $R^4$, $R^{14}$, $R^{15}$, $R^{16}$ and $R^{17}$ are as defined above.

6. Salt according to claim 1, wherein the cation is a benzimidazolidinium cation of the general formula

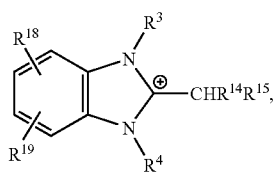
(VII)

wherein $R^3$, $R^4$, $R^{14}$ and $R^{15}$ are as defined above and
$R^{18}$ and $R^{19}$ stand, independently from one another, for an H atom, F, Cl, a linear or branched alkyl group with 1 to 20 C atoms, an aryl group or a benzyl group.

7. Salt according to claim 4, wherein the groups $R^3$ and $R^4$ are different.

8. Salt according to claim 1, wherein the cation is an N-organo-pyridinium ion of the general formula

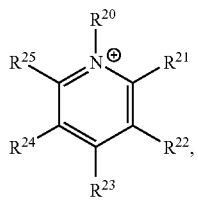
(IX)

wherein
$R^{20}$ represents a linear or branched alkyl group with 1 to 20 C atoms, an aryl or a benzyl group, and
$R^{21}$, $R^{22}$, $R^{23}$, $R^{24}$ and $R^{25}$ represent, independently from one another, an H atom, F, Cl or a linear or branched alkyl group with 1 to 20 C atoms.

9. Method for producing salts, comprising an anion of the general formula

(I)

wherein $R^1$=—$SO_2$—$R^2$, wherein
$R^2$ represents a branched or unbranched alkyl group with 1 to 20 C atoms or an aryl group or benzyl group and this alkyl group, benzyl group or aryl group is non-fluorinated, partially or completely fluorinated; wherein $R^2$ is not $CF_3$;
wherein the conjugate acid

(X)

of the anion according to formula (I) is reacted with the conjugate compound of a cation in an organic solvent, and wherein the cation is chosen from the group of phosphonium ions, guanidinium ions, imidazolium ions, imidazolidinium ions, benzimidazolium ions and N-organo-pyridinium ions.

10. Method according to claim 9, wherein the organic solvent is selected from the group consisting of purely aliphatic, unsaturated and aromatic hydrocarbons, for example, toluol, partially or completely halogenated hydrocarbons (e.g. chlorobenzene, chloroform, tetrachlorocarbon, CFC, FC, frigenes), organic amines, ethers, alcohols (optionally mixed with water), ketones, DMF, DMSO, HMPT, organic carbonates, carboxylic acid amides and carboxylic acid esters and tetraalkylureas.

11. Method according to claim 9, wherein the cation is a guanidinium ion and the guanidium salt is produced through reaction of the conjugate acid of the anion with a guanidinium ion through ion exchange.

12. Method according to claim 9, wherein the cation is a phosphonium ion and the phosphonium salt is produced through reaction of the conjugate acid of the anion with an alkyl-alkylidene phosphorane or aryl-alkylidene phosphorane.

13. Method according to claim 9, wherein the cation is a 2-alkyl-substituted imidazolium cation, imidazolidinium cation or benzimidazolium cation and the salt is produced through reaction of the conjugate acid of the anion with a ketene N,N-diacetal, chosen from the group of 1,3-dialkyl-2-alkylene-imidazoline, 1,3-diaryl-2-alkylene-imidazoline, 1,3-dialkyl-2-alkylene-benzimidazole and 1,3-dialkyl-2-benzilydene-imidazole.

14. Method according to claim 9, wherein the cation is an N-organo-pyridinium cation and the salt is produced through reaction of the conjugate acid of the anion with a salt comprising the N-organo-pyridinium cation.

15. Salt according to claim 5, wherein the groups $R^3$ and $R^4$ are different.

16. Salt according to claim 6, wherein the groups $R^3$ and $R^4$ are different.

17. In a method of using a salt as a component of an ionic liquid for electrolyte systems in batteries, galvanic elements and rechargeable battery packs, the improvement comprising using a salt comprising:
a) an anion of the general formula

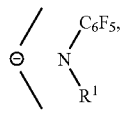
(I)

wherein
represents $R^1$=—$SO_2$—$R^2$, wherein
$R^2$ represents a branched or unbranched alkyl group with 1 to 20 C atoms or an aryl group or benzyl group and this alkyl group, benzyl group or aryl group is non-fluorinated, partially or completely fluorinated; wherein $R^2$ is not $CF_3$; and
b) a cation, wherein said cation is chosen from the group of phosphonium ions, guanidinium ions, imidazolium ions, imidazolidinium ions, benzimidazolium ions and N-organo-pyridinium ions.

18. The method of claim 17, wherein the battery is a lithium ion rechargeable battery.

19. In a method of using a salt as a solvent for multiphase catalysts, the improvement comprising using a salt comprising:
a) an anion of the general formula

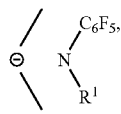
(I)

wherein
$R^1$=—$SO_2$—$R^2$, wherein
$R^2$ represents a branched or unbranched alkyl group with 1 to 20 C atoms or an aryl group or benzyl group and this alkyl group, benzyl group or aryl group is non-fluorinated, partially or completely fluorinated; $R^2$ is not $CF_3$; and
b) a cation, wherein said cation is chosen from the group of phosphonium ions, guanidinium ions, imidazolium ions, imidazolidinium ions, benzimidazolium ions and N-organo-pyridinium ions.

20. In a method of using a salt as a nonaqueous electrolyte, the improvement comprising using a salt comprising:
a) an anion of the general formula

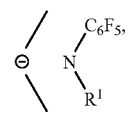
(I)

wherein
$R^1$=—$SO_2$—$R^2$, wherein
$R^2$ represents a branched or unbranched alkyl group with 1 to 20 C atoms or an aryl group or benzyl group and this alkyl group, benzyl group or aryl group is non-fluorinated, partially or completely fluorinated; wherein $R^2$ is not $CF_3$; and
b) a cation, wherein said cation is chosen from the group of phosphonium ions, guanidinium ions, imidazolium ions, imidazolidinium ions, benzimidazolium ions and N-organo-pyridinium ions.

21. In a method of using a salt as a mobile and/or stationary phase in chromatography, the improvement comprising using a salt comprising:
a) an anion of the general formula

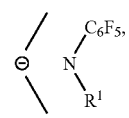
(I)

wherein
$R^1$=—$SO_2$—$R^2$, wherein
$R^2$ represents a branched or unbranched alkyl group with 1 to 20 C atoms or an aryl group or benzyl group and this alkyl group, benzyl group or aryl group is non-fluorinated, partially or completely fluorinated; wherein $R^2$ is not $CF_3$; and
b) a cation, wherein said cation is chosen from the group of phosphonium ions, guanidinium ions, imidazolium ions, imidazolidinium ions, benzimidazolium ions and N-organo-pyridinium ions.

\* \* \* \* \*